(12) United States Patent
Broadbent et al.

(10) Patent No.: US 6,723,834 B1
(45) Date of Patent: Apr. 20, 2004

(54) REACTIVE DYE COMPOUNDS

(75) Inventors: Peter Jeffrey Broadbent, Knaresborough (GB); Dong Wei He, Morley (GB); David Malcolm Lewis, Otley (GB); Gilles Yves Marie Fernand Ganain, London (GB); Taher Iqbal Yousaf, Egham (GB)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 10/089,346

(22) PCT Filed: Sep. 29, 2000

(86) PCT No.: PCT/US00/26976
§ 371 (c)(1),
(2), (4) Date: Mar. 27, 2002

(87) PCT Pub. No.: WO01/25339
PCT Pub. Date: Apr. 12, 2001

(30) Foreign Application Priority Data

| Oct. 1, 1999 | (GB) | 9923330 |
| Mar. 22, 2000 | (GB) | 0006968 |
| Apr. 25, 2000 | (GB) | 0009845 |

(51) Int. Cl.$^7$ .............. C09B 62/022; C09B 67/24; D06P 1/38
(52) U.S. Cl. .............. 534/588; 534/596; 534/617; 534/633; 534/638; 540/125; 540/126; 544/187; 544/189; 544/208; 544/211; 544/311; 544/317; 544/321; 544/354; 8/428; 8/524; 8/528; 8/543; 8/549
(58) Field of Search ................. 534/588, 596, 534/617, 633, 638; 540/125, 126; 544/187, 189, 208, 211, 311, 317, 321, 354; 8/428, 524, 528, 543, 549

(56) References Cited

U.S. PATENT DOCUMENTS

| 3,116,275 A | 12/1963 | Gamlen et al. |
| 3,377,336 A | 4/1968 | Siegel et al. |
| 3,433,781 A | 3/1969 | Ackerman et al. |
| 3,522,246 A | 7/1970 | Siegel et al. |
| 3,527,760 A | 9/1970 | Edgar et al. |
| 3,873,513 A | 3/1975 | Kullman et al. |
| 4,092,478 A | 5/1978 | Plant et al. |
| 4,098,784 A | 7/1978 | Swidler et al. |
| 4,139,345 A | 2/1979 | Crabtree et al. |
| 4,150,021 A | 4/1979 | Swidler et al. |
| 4,832,698 A | 5/1989 | Ikeou et al. |
| 4,855,411 A | 8/1989 | Thompson et al. |
| 4,898,933 A | 2/1990 | Schläfer et al. |
| 5,037,449 A | 8/1991 | Hoegerle et al. |
| 5,175,263 A | 12/1992 | Schläfer |
| 5,548,071 A | 8/1996 | Deitz et al. |
| 5,766,267 A | 6/1998 | Schumacher et al. |
| 5,877,310 A | 3/1999 | Reddington et al. |
| 6,350,862 B1 | 2/2002 | Brock et al. |
| 6,398,822 B1 | 6/2002 | Brock et al. |

FOREIGN PATENT DOCUMENTS

| CA | 771632 | 11/1967 |
| DE | 33 35 956 A1 | 4/1985 |
| DE | 196 45 601 A | 5/1998 |
| EP | 0 260 806 A2 | 3/1988 |
| EP | 0 735 107 A2 | 9/1990 |
| EP | 0 418 623 A1 | 3/1991 |
| FR | 1 274 732 A | 2/1962 |
| GB | 949 316 A | 2/1964 |
| GB | 1 020 304 | 2/1966 |
| GB | 1 060 734 | 3/1967 |
| GB | 1 275 944 | 6/1972 |
| GB | 1 414 420 A | 11/1975 |

(List continued on next page.)

OTHER PUBLICATIONS

I. Grabtchev "The Synthesis and Properties of some Triazine–stilbene Fluorescent Brighteners", Dyes Pigm., 1994, pp. 249–254, 25.
The Journal of Macromelecular Chemistry, 1976, 50, pp. 1–8, 728.
The Journal of Macromelecular Chemistry, 1977, 64, pp. 205–210, 951.
S. Horrobin, "The Hydrolysis of Some Chloro–1,3,5–Triazines", The Journal of the Chemical Society, 1963, pp. 4130–4144.
F. Lehr, "Synthesis and Application of Reactive Dyes with Heterocyclic Reactive Systems," Jan. 19, 1990, pp. 239–263.

*Primary Examiner*—Fiona T. Powers
(74) *Attorney, Agent, or Firm*—Jenkins, Wilson & Taylor, P.A.

(57) ABSTRACT

A reactive dye compound comprising:
  (a) at least one chromophore moiety;
  (b) at least one nitrogen-containing heterocycle
  (c) a linking group to link each chromophore moiety to each nitrogen-containing heterocycle;
  characterized in that at least one nitrogen-containing heterocycle is substituted with at least one Y group wherein Y is derived from a hydrated aldehyde, a hydrated ketone, a hydrated alpha-hydroxy ketone, or the hydrated form of formic acid and linked via one of its oxygen atoms to the nitrogen-containing heterocycle thereby forming a hemiacetal.

The compounds herein have high Exhaustion Values (E), high Fixation Values (F) and high Efficiency Values (T) and show significant improvements in terms of reducing spent dyestuff in effluent, increasing dye affinity to the substrate, increasing the dye-substrate covalent bonding, increasing the ability to dye substrates at room temperature, decreasing the amount of dye that is removed during the post dyeing "soaping off process" and therefore simplifying the post dyeing "soaping off process" traditionally associated with dyeing cotton with fibre reactive dyes and reduction of staining of adjacent white fabrics. In addition, the compounds prepared above provide more intense dyeings and require less levels of salt for dyeing cotton substrates.

38 Claims, No Drawings

FOREIGN PATENT DOCUMENTS

| | | |
|---|---|---|
| JP | 60 208 367 | 10/1985 |
| JP | 63 006 181 | 1/1988 |
| WO | WO-96/02593 | 2/1996 |
| WO | WO 97 19188 A | 5/1997 |
| WO | WO 99/51685 | 10/1999 |
| WO | WO 99/51686 | 10/1999 |
| WO | WO 99/51689 | 10/1999 |
| WO | WO 00/69973 | 11/2000 |
| WO | WO 00/69974 | 11/2000 |
| WO | WO 01/25336 | 4/2001 |
| WO | WO 01/25337 | 4/2001 |
| WO | WO 01/25338 | 4/2001 |

REACTIVE DYE COMPOUNDS

TECHNICAL FIELD

The present invention relates to reactive dye compounds. In particular the present invention relates to reactive dye compounds having improved dye-bath Exhaustion (E) and improved dye-fibre covalent Fixation (F).

BACKGROUND OF THE INVENTION

Reactive dye compounds are known in the art for dyeing various substrates. Such substrates include for example proteinaceous materials such as keratin, e.g. found in hair, skin and nails and various animal body parts such as horns, hooves and feathers, and other naturally occurring protein containing materials, e.g. silk and saccharide-derived materials such as those derived from cellulose or cellulose derivatives, e.g. natural products such as cotton, and synthetic fibres such as polyamides.

Examples of classes of such reactive dyes which are well known in the art include dyes containing a mono- or dichloro- or fluoro-1,3,5-triazinyl group, trichloro or mono- or di-fluoro-pyrimidyl group, beta-halogen-propionyl group, beta-halogenoethyl-sulphonyl group, beta-halogenoethylsulphamyl group, chloroacetyl amino, beta-(chloro-methyl)-beta-sulphatoethylsulphamyl group, or a vinyl sulphonyl group.

In the case of the dyes containing a triazinyl group or a pyrimidyl group, in place of the reactive halogen atoms one can use other groups which dissociate in the presence of alkali. Canadian Patent 771632, for example, discloses examples of such other groups including sulphonic acid, thiocyanate, sulphophenoxy, sulphophenyl thio, nitrosulphophenoxy groups, and quaternary ammonium groups.

"The Synthesis and Properties of some Triazine-Stilbene Fluorescent Brighteners", I. Grabtchev, discloses the synthesis of certain triazine stilbene fluorescent brighteners containing methacrylic groups.

The Journal of Macromoleular Chemistry 64 (1977), 205–210 (Nr. 951) discloses the polymerisation of acrylonitrile in dimethylformamide in the presence of some unsaturated triazine derivatives. The Journal of Macromolecular Chemistry 50 (1976) 1–8 (Nr.728) discloses the polymerization of styrene in the presence of some coloured anthraquinone and azoderivatives of 1,3,5-triazine, containing a group able to copolymerize.

The Journal of the Chemical Society, 1963, pages 4130–4144, "The Hydrolysis of Some Chloro-1,3,5-Triazines" by S. Horrobin, discloses that dichloro-m-sulphoanilinotriazine is rapidly hydrolysed in acetate (pH 4.7) or phthalate (pH 4.0) buffers.

There are many different types of commercially-available reactive dyes for dyeing cellulosic and polyamide-type substrates. However, a critical problem still facing the textile dye industry today is the significant level of dyestuff material which remains in the effluent waste water after the dyeing process is finished. The industry measure for this problem is known as dye-bath Exhaustion (E). A high Exhaustion value for a particular dye compound means that a low level of spent dye remains in the effluent after the dyeing process is complete, while a low Exhaustion value means that a high level of spent dye remains in the effluent. There is clearly a need therefore for new dye compounds which have higher Exhaustion Values compared with commercially available dye compounds, and which provide benefits in terms of reducing levels of spent dyestuff in effluent water.

As well as having a high Exhaustion Value, it is also important for a dye compound to have a high dye-fibre covalent Fixation Value (F). The Fixation Value (F) of a reactive dye compound is a measure of the extent of covalent bonding with the substrate based on the dye originally absorbed during the dyeing process. Thus 100% Fixation means that 100% of the absorbed dye covalently bonds to the substrate. Thus, there is clearly a need to provide dye compounds having increased Fixation Values. A high Fixation Value can result in a simplification of the post dyeing "soaping off process" traditionally associated with fibre reactive dye compounds. In particular, a high Fixation Value can result in a reduced time spent on the "soaping off process" together with a reduced cost.

It has now been surprisingly found that a new class of fibre reactive dye compounds comprising a nitrogen-containing heterocycle substituted with at least one substituent derived from a hydrated aldehyde, a hydrated ketone, a hydrated alpha-hydroxy ketone, such as for example the hydrated forms of sucrose or glucose and the hydrated form of formic acid, and linked via one of its oxygen atoms to the nitrogen-containing heterocycle thereby forming a hemiacetal, exhibit significantly increased values of Exhaustion (E) and Fixation (F). These dyes can be used on a wide variety of substrates. They are particularly useful for cellulosic substrates, such as cotton, and materials such as keratin, hair, wool and silk, and show significant improvements in terms of reducing spent dyestuff in effluent, increasing dye affinity to the substrate, increasing the efficiency of the dye-substrate covalent reaction, and simplifying the post dyeing "soaping off process" traditionally associated with reactive dyes. In addition, the compounds of the present invention provide significantly more intense dyeings, and can be used for both high and low temperature dyeing, hence reducing the cost of the dyeing process. Furthermore, the compounds of the present invention can be used together with specific chromophores for cellulose substrate dyeing leading to significantly reduced levels of salt needed for dyeing.

SUMMARY OF THE INVENTION

According to the present invention there is provided a reactive dye compound comprising:
(a) at least one chromophore moiety;
(b) at least one nitrogen-containing heterocycle
(c) a linking group to link each chromophore moiety to each nitrogen-containing heterocycle;
characterised in that at least one nitrogen-containing heterocycle is substituted with at least one Y group wherein Y is derived from a hydrated aldehyde, a hydrated ketone, a hydrated alpha-hydroxy ketone, or the hydrated form of formic acid, and linked via one of its oxygen atoms to the nitrogen-containing heterocycle thereby forming a hemiacetal.

The compounds of the present invention exhibit increased Exhaustion (E) and Fixation (F) values and provide improvements in terms of reducing spent dyestuff in effluent, increasing dye affinity to the substrate, increasing the efficiency of the dye-substrate covalent reaction, ability to carry out the long-liquor dyeing process at room temperature as well as at elevated temperatures, and simplifying the post dyeing "soaping off process" traditionally associated with fibre reactive dyes. In addition, the compounds of the present invention provide significantly more intense dyeings, i.e. greater colour intensity in the dyed substrate, without compromising levelness. Typical Exhaustion Values for the compounds and products herein are greater than 95%. Typical Fixation Values for the compounds and products herein are greater than 95%.

DETAILED DESCRIPTION OF THE INVENTION

As used herein the term "reactive dye" means a dye containing one or more reactive groups, capable of forming covalent bonds with the substrate to be dyed, or a dye which forms such a reactive group in situ.

As used herein the term "Exhaustion" in relation to reactive dyes means the percentage of dye which is transferred from a solution of the dye to the substrate to be treated at the end of the dyeing process, before rinsing and soaping. Thus 100% Exhaustion means that 100% of the dye is transferred from the dye solution to the substrate. Typical Exhaustion Values for the dye compounds herein are >95%.

As used herein the term "Fixation" in relation to reactive dyes means the percentage of dye which covalently bonds with the substrate, based on the dye originally absorbed during the dyeing process. Thus 100% Fixation means that 100% of the dye absorbed is covalently bonded with the substrate. Typical Fixation Values for the dye compounds herein are 95%.

The total efficiency of reactive dyes can be measured by their Efficiency Value (T) which can be calculated from the Exhaustion Value (E) and Fixation Value (F) using the following equation:

$$\%T=(F\times E)/100$$

The compounds of the present invention comprise a chromophoric moiety and a nitrogen-containing heterocycle linked via a linking group. The nitrogen-containing heterocycle is substituted by at least one Y group wherein Y is derived from a hydrated aldehyde, a hydrated ketone, a hydrated alpha-hydroxy ketone or the hydrated form of formic acid, and linked via one of its oxygen atoms to the nitrogen-containing heterocycle thereby forming a hemiacetal.

Chromophoric Moiety

The reactive dye compounds herein can comprise one or more chromophoric moieties (D or D'). In reactive dye compounds comprising two or more chromophoric moieties these can be the same or different. Preferably the reactive dye compounds herein comprise from one to three chromophoric moieties.

Any chromophoric moieties suitable for use for dyeing substrates can be used in the present invention. The term chromophore as used herein means any photoactive compound and includes any coloured or non-coloured light absorbing species, e.g. fluorescent brighteners, UV absorbers, IR absorbing dyes.

Suitable chromophoric moieties for use in the dye compounds herein include the radicals of monoazo, disazo or polyazo dyes or of heavy metal complex azo dye derived therefrom or of an anthraquinone, phthalocyanine, formazan, azomethine, dioxazine, phenazine, stilbene, triphenylmethane, xanthene, thioxanthene, nitroaryl, naphthoquinone, pyrenequinone or perylenetetracarbimide dye.

Suitable chromophoric moieties for use in the dye compounds herein include those disclosed in EP-A-0,735,107 (Ciba-Geigy), incorporated herein by reference, including the radicals described therein which contain substituents customary for organic dyes, such as sulphonate substituents which enhance the water-soluble properties of the dye compound.

Most preferred chromophoric D or D' groups for use herein are polysulphonated azo chromophores such as those present in Procion (RTM) dyes commercially available from BASF, Drimalan (RTM) dyes commercially available from Clariant, Drimarene (RTM) dyes commercially available from Clariant, Levafix (RTM) dyes commercially available from Dystar and Sumifix supra (RTM) dyes commercially available from Sumitomo.

Nitrogen-containing Heterocycle

The reactive dyes of the present invention comprise at least one nitrogen-containing heterocyclic moiety. In reactive dye compounds containing two or more nitrogen-containing heterocycles these can be the same or different. Preferably the reactive dye compounds herein comprise from one to three nitrogen-containing heterocycles. At least one of the nitrogen-containing heterocycle moieties herein is substituted with at least one Y group defined below.

Suitable nitrogen-containing heterocycles for use herein include monocyclic, bicyclic or polycyclic, unsaturated heterocycles containing at least one nitrogen heteroatom. When monocyclic rings are used, they are preferably selected from unsaturated rings having from about 3 to about 7 ring atoms, especially 5 or 6 ring atoms, comprising from about 1 to about 3 nitrogen heteroatoms, preferably 2 or 3 nitrogen heteroatoms. When bicyclic heterocycles are used, they preferably comprise an unsaturated nitrogen containing heterocycle having 3 to 7 ring atoms, preferably an unsaturated nitrogen containing heterocycle having 5 or 6 ring atoms comprising 1 or 2 nitrogen atoms, fused to a 5 to 7 membered carbocycle preferably a 6-membered unsaturated carbocycle. When bicyclic heterocycles are used, the oxy- or thio-carbonyl substituents are preferably attached to the nitrogen-containing heterocyclic ring.

Preferred for use herein are 5 or 6 membered unsaturated nitrogen-containing monocyclic heterocyclic rings comprising 2 or 3 nitrogen heteroatoms or bicyclic rings containing a 5 or 6 membered unsaturated heterocyclic ring containing 2 nitrogen heteroatom fused to a 6 membered unsaturated carbocycle.

Examples of suitable heterocycles for use herein include, but are not necessarily limited to triazine, pyrimidine, quinoxaline, pyrimidinone, phthalazine, pyridazone and pyrazine.

Preferred for use in the compounds herein are triazine, pyrimidine and quinoxaline.

Linking Moiety

The compounds herein further comprise a linking moiety to link each nitrogen-containing heterocycle to each chromophoric moiety. Any linking moieties suitable for use in dyeing substrates can be used in the present invention. Preferably the linking moiety is selected from NR, NRC=O, C(O)NR, NRSO$_2$ and —SO$_2$NR wherein R is H or C$_1$–C$_4$ alkyl which can be substituted by halogen, preferably fluorine or chlorine, hydroxyl, cyano, C$_1$–C$_4$ alkoxy, C$_2$–C$_5$ alkoxycarbonyl, carboxyl, sulfamoyl, sulfo or sulfato. When the heterocycle is a triazine or pyrimidine a preferred linking moiety is NR, preferably where R is H or C1–C4 alkyl, more preferably where R is H or CH$_3$, especially H. When the heterocycle is quinoxaline or phthalazine, a preferred linking moiety is NRC=O, where R is H or C1–C4 alkyl, more preferably where R is H or CH$_3$, especially H.

Substituent Y

The nitrogen-containing heterocycle is substituted with at least one Y group wherein Y is is derived from a hydrated aldehyde, a hydrated ketone, a hydrated alpha-hydroxy ketone or the hydrated form of formic acid, and linked via one of its oxygen atoms to the nitrogen-containing heterocycle thereby forming a hemiacetal.

Particularly preferred Y groups herein are the hydrated form of an aldehyde or ketone. Preferably the Y group is derived from a hydrated from of a reducing sugar selected from an aldose or a ketose.

Suitable aldose materials for use herin include an aldotriose, an aldotetrose, an aldopentose, an aldohexose, an aldoheptose and an aldooctose, and mixtures thereof. A preferred aldose material for use herein is an aldopentose material, preferably selected from ribose, xylose, arabinose, deoxyribose and fructose and mixtures thereof. Another preferred aldose material for use herein is an aldohexose material, preferably selected from glucose, galactose, talose, mannose, altrose, allose and rhamnose, and mixtures thereof. Most preferred for use herein are the hydrated forms of glucose, sucrose and fructose. Hydrated isomers of sucrose or glucose can be formed by acid hydrolysis of sucrose and glucose, respectively. A preferred Y group herein is a group derived from the hydrated isomer of sucrose or glucose, namely —O—(CHOH)$_4$(CHOHCH$_2$OH).

Suitable ketose materials for use herein include an aldotetrulose, an aldopentulose, an aldoheptulose, an aldooctulose and mixtures thereof.

Other suitable aldehyde and ketone materials which can be converted to their hydrated form via acid hydrolysis include, but are not limited to, furfural, glucosamine, 1-glycine aldehyde, 1-mannose, 1-galactose, piperidone, 2-methylene-3-quinuclidinone dihydrate HCl, ascorbic acid, paraformaldehyde, glyoxylic acid, glyoxal, glutaraldehyde, chloral, dihydroxy tartaric acid, 2-2-dihydroxy-5-methoxy-1,5-methoxy-3-indandione hydrate (ninhydrin), 2-2-dihydroxy-1H-benz(F)indene-1,3(2H)-dione hydrate, mesoxalic acid, alloxan, pyruvic acid, glyceraldehyde, 2,5-piperazine-dione, d-erythrose, d-threose, d-ribose, d-arabinose, d-xylose, d-lyxose, d-ribulose, and the compound having the structure:

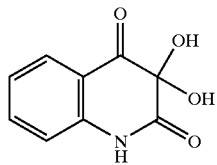

Particularly preferred Y groups herein are groups derived from saccharide molecules such as sucrose and glucose, and the like, which have been hydrolysed to their hydrated forms. A preferred Y group herein is a group derived from the hydrated isomer of sucrose or glucose, namely —O—(CHOH)4(CHOHCH2OH). Hydrated isomers of sucrose and glucose can be formed by acid hydrolysis of sucrose and glucose, respectively. When saccharides such as sucrose and glucose are subjected to acid hydrolysis they can also form a polymeric structure and hence in that case the Y group would also be polymeric. Another preferred Y group is derived from the hydrated form of formic acid, (e.g. —CH(OH)(OH)), which can also be polymeric.

Preferred reactive dye compounds of the present invention may be represented by the following formula (I):

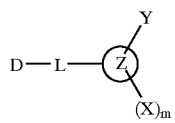

wherein:

D is a chromophoric group;

L is a linking moiety selected from NR, N(C=O)R, N(SO$_2$)R;

R is H or $C_1$–$C_4$ alkyl which can be substituted by halogen, hydroxyl, cyano, $C_1$–$C_4$ alkoxy, $C_2$–$C_5$ alkoxycarbonyl, carboxyl, sulfamoyl, sulfo, sulfato;

Z is a nitrogen-containing heterocycle;

Y is as defined above;

X is selected from Y (i.e. bis-saccharide compounds), thio-derivatives, halogen (preferably fluorine and chlorine), amines, alkoxy groups, carboxylic acid groups, CN, N$_3$, quaternized nitrogen derivatives, Q+, and oxy- or thio-carbonyl derivatives having the formula —A(CO)R* wherein A is selected from O or S, where R* is an organic residue which contains at least one nucleophilic group, wherein the nucleophilic group is preferably selected from OH, NH$_2$, SH, COOH, —N=, NHR$^1$ and NR$^1$R$^2$ wherein R$^1$ and R$^2$ may be the same of different and may be selected from $C_1$–$C_4$ alkyl;

m is 1 or 2 (depending on the Z group, for example m is 1 when Z is triazine and m is 2 when Z is pyrimidine).

Suitable thio-derivatives for use herein include, but are not necessarily limited to groups having the formula SR' wherein R' is selected from H or alkyl or preferably short chain alkyl (preferably less than about 6 carbon atoms), alkanol, alkyl carboxylate, alkylamide, alkylsulphonate, alkyl phosphonate, alkyl thiosulphonate, alkylamine, alkyl thiosulphate, aryl sulphonate, aryl carboxylate, aryl phosphate, aryl amine, cyanates, sulphonates, branched alkyl thio carboxylates, branched alkanol thiols, guanides, alkyl-α-amino-α-carboxylate, (di) thio alkyl esters of glycerol, alkyl thiol alkyl esters of glycerol, alkyl esters, mono thio diesters, thiol alkyl esters of ethylene glycol, alkyl thiol alkyl ester of ethylene glycol and alkyl thiolipoates. Preferably R' is selected from alkyl carboxylates, alkanols and alkylamines.

Examples of suitable thio-derivatives include SR' groups where R' is selected from $C_1$–$C_4$ alkyl, $(CH_2)_n COOH$, $(CH_2)_n CONH_2$, $(CH_2)_n SO_3 H$, $(CH_2)_n COOM$, $(CH_2)_n PO_3 H$, $(CH_2)_n OH$, $(CH_2)_n SSO_3^-$, $(CH_2)_n NR"_2$, $(CH_2)_n N^+R"_3$, $PhSSO_3^-$, $PhSO_3 H$, $PhPO_3 H$, $PhNR"_2$, $PhN^+R"_3$, —CN, $SO_3^-$, $(CH_2)_2 CH(SH)R"(CH_2)_3 COOH$, —$CH_2 CHOHCH_2 SH$, and

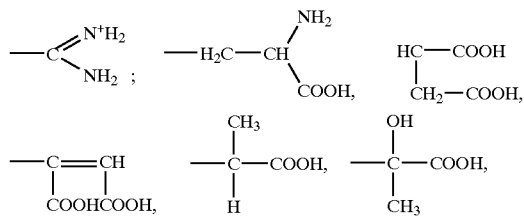

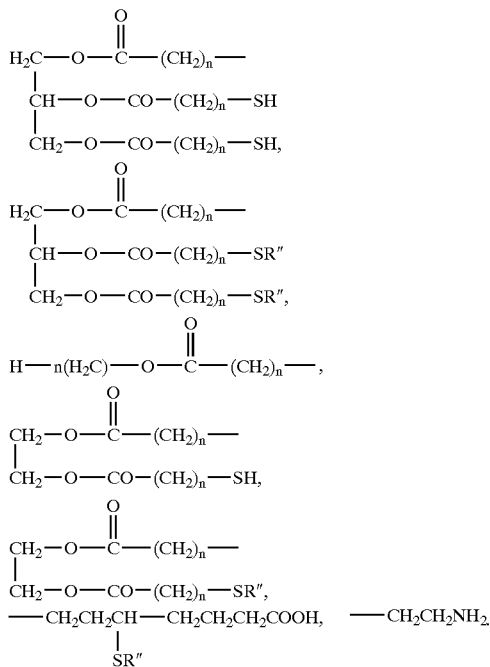

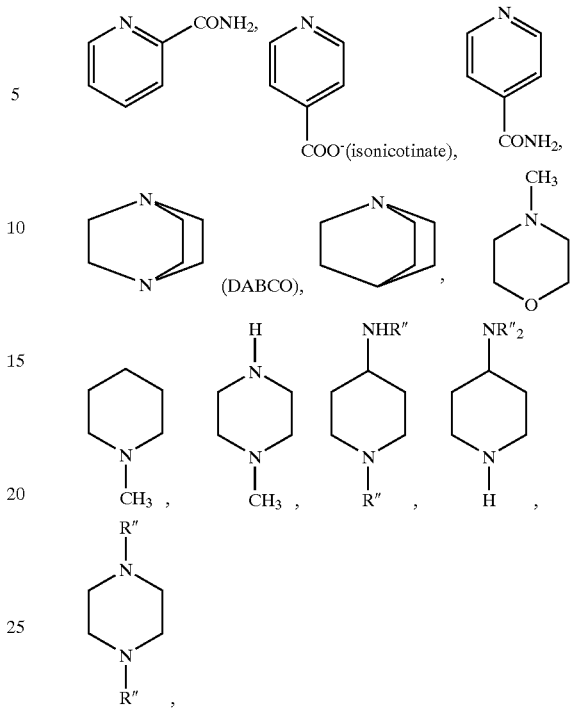

n is an integer in the range of 1 to 4 wherein within the same molecule n is not necessarily the same integer; and M is a cation of alkaline earth metal, alkali metal, $NH_4^+$ or $NR''_3^+$ and wherein R" is $C_1$–$C_4$ alkyl.

Preferred thio-derivatives for use herein have the formula SR' wherein R' is $(CH_2)_nCOOH$, $(CH_2)_nOH$, and $(COOH)CH_2CH_2(COOH)$, wherein n is an integer from 1 to 4.

Especially preferred for use herein are thioglycolate (R'=$CH_2COOH$) thioethanol (R'=$(CH_2)_2OH$) and thiosuccinate (R'=$(COOH)CH_2CH_2(COOH)$), especially thioglycolate.

Suitable quaternized nitrogen derivatives for use herein can be represented by Q+ wherein Q is selected from amines, saturated or unsaturated, substituted or unsubstituted nitrogen containing heterocycles having from about 3 to about 8 ring members and comprising at least one nitrogen heteroatom. Preferred substituents are carboxylates, amides, $C_1$–$C_4$ alkyl and alkyl carboxylates.

Particularly preferred for use herein are Q groups selected from:

$NR''_3$,

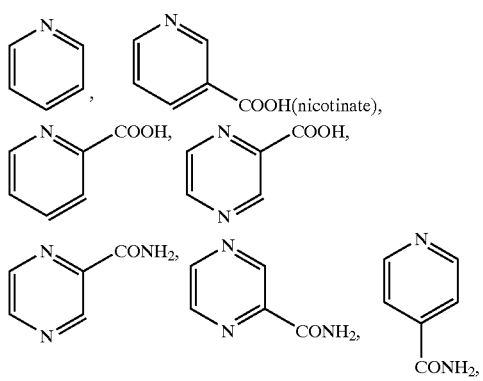

$(CH_3)_2N-NH_2$;
$N(CH_3)_2CH_2COOH$ (dimethylaminobetaine);
$N(CH_3)_2(CH_2)_nNH_2$
$N(CH_3)_2(CH_2)_nN^+R''_3$;
$N(CH_3)_2CH_2CONH_2$;
wherein R" is $C_1$–$C_4$ alkyl and n is an integer of from 1 to 4.

Particularly preferred quaternized nitrogen derivatives for use herein are nicotinate, diazabicyclooctane (DABCO), dimethylaminobetaine and isonicotinate, especially nicotinate.

The quaternized nitrogen derivative is attached to the nitrogen-containing heterocycle via its quaternary nitrogen atom.

Oxy- or Thio-carbonyl Derivative

Suitable oxy- or thio-carbonyl derivatives for use herein are those having the formula—A(C═O)R* wherein A is selected from O, S or Se, preferably S or O, more preferably O, wherein R* is an organic residue which comprises at least one nucleophilic group. As used herein the term "nucleophilic group" means a negative ion or any neutral molecule that has an unshared electron pair. Preferred nucleophilic groups herein can be selected from OH, $NH_2$, SH, COOH, —N═, $NHR^1$ and $NR^1R^2$ wherein $R^1$ and $R^2$ may be the same or different and may be selected from $C_1$–$C_4$ alkyl.

Suitable R* groups for use herein are alkyl or aryl residues which contain at least one nucleophilic group. Preferably the R* groups herein are selected from the following groups each substituted with or containing at least one nucleophilic group: substituted or unsubstituted, straight chain or branched chain $C_1$–$C_8$ alkyl, substituted or unsubstituted straight chain or branched chain $C_2$–$C_8$ alkenyl having at least one olefinic group, substituted or unsubstituted, saturated or unsaturated or aromatic 3–9 atom monocyclic carbocycle or substituted or unsubstituted, saturated or unsaturated or aromatic 7–17 polycyclic carbocycle, substituted or unsubstituted, saturated or unsaturated or aromatic 3–9 atom monocyclic heterocycle or substituted or unsubstituted, saturated or unsaturated or aromatic 7–17 atom polycyclic heterocycle, wherein said heterocycles each have one or more heteroatoms selected from O, N or S.

In the definition of R* above, where the term "substituted" is used such substitution may be with one or more substituents. Such substituents include, but are not limited to, those listed in C. Hansch and A. Leo, *Substituent Constants for Correlation Analysis in Chemistry and Biology* (1979), hereby incorporated by reference herein. Preferred substituents include, but are not limited to, alkyl, alkenyl, alkoxy, hydroxy, oxo, amino, aminoalkyl (e.g.aminomethyl, etc.), cyano, halo, carboxy, alkoxyacetyl (e.g. carboethoxy, etc.), thio, aryl, cycloalkyl, heteroaryl, heterocycloalkyl, (e.g.piperidinyl, morpholinyl, piperazinyl, pyrrolidinyl, etc.), imino, thioxo, hydroxyalkyl, aryloxy, arylalkyl, and combinations thereof.

Preferred R* groups for use herein include, but are not limited to, $CF_3$, $(CH_2)_nSH$, $(CH_2)_nNH_2$, $CH(CH_3)OH$, $C(OH)(CH_2COOH)_2$, $CH_2C(OH)(CO_2H)CH_2COOH$, $(CH_2)_nNHR_1$, $CH_2NR_1R_2$, $CH_2NHNH_2$, $CH_2NHOH$, $CH_2SMe$, $CH(NH_2)(CH_2)_n(COOH)$, $CH(NH_2)CH_2SMe$, $CH(NH_2)CH_2SSCH_2CH(NH_2)COOH$, 2-aminophenyl, 2-hydroxynaphthyl, 2-pyrrolidyl, $CH_2SSCH_2CO_3^-$, $(CH_2)_n—SO_3^-$, $CH(NH_2)CH_2SO_3H$, $C_6H_4OH$, $C_6H_4COOH$, $C_6H_4NH_2$, $C_5H_4N$, $(CH_2)_nC_5H_4N$, $CH(R\#)NH_2$, $(CH_2)_n—SSO_3^-$, $(CH_2)n-S—S—(CH_2)_n$, $—C(OH)(H)C(OH)(H)COOH$, $—C(OH)(H)CH_2COOH$, $—C(OH)(COOH)CH_2COOH$, $CH_2(H)(OH)COOH$, derivatives of hydroxy carboxylic acid polymerisation, e.g. in the case of lactic acid dimerisation R* is $CH(CH_3)O(CO)CH(CH_3)OH$, R* groups derived from peptide or polypeptide and attached to the heterocyclic group via their terminal carboxylic group, wherein $R_1$ and $R_2$ is independently selected from $C_1$–$C_4$ alkyl, wherein n is an integer in the range of 1 to 4 wherein within the same molecule n is not necessarily the same integer and where R# corresponds to an amino acid sidechain. For examples of such amino acids, cf. "Organic Chemistry" by Graham Solomons, 5th Edition, Wiley, N.Y., 1992, p1094–1095.

Preferred R* groups for use herein are selected from $(CH_2)_nSH$, $(CH_2)_nNH_2$, $C_5H_4N$, $CH(CH_3)OH$, $C(OH)(CH_2COOH)_2$, $CH(R\#)NH_2CH_2C(OH)(COOH)CH_2COOH$, $CH(CH_3)OH$, $CH(OH)CH_2COOH$, $CH_2C(H)(OH)COOH$, $C(H)(OH)C(H)(OH)COOH$, $C_6H_4OH$, $C_6H_4NH_2$ and $C_5H_4N$.

Particularly preferred R* groups herein are groups derived from hydroxy carboxylic acids such as citric acid, lactic acid, tartaric acid, malic acid, salicylic acid, and the like, including structural isomers thereof (e.g. in the case of citric acid R* can be $C(OH)(CH_2COOH)_2$ and $CH_2C(OH)(COOH)CH_2COOH$) and polymers thereof (e.g. in the case of polymerisation of two lactic acid molecules R* is $CH(CH_3)O(CO)CH(CH_3)OH$.

Particularly preferred R* group from the viewpoint of providing reactive dye compounds having excellent dye properties are those derived from citric acid, including $C(OH)(CH_2COOH)_2$ and $CH_2C(OH)(COOH)CH_2COOH$. It will be understood by those skilled in the art that in the case of unsymmetrical compounds having more than one carboxylic acid group, for example, citric acid and malic acid, that a mixture of dye compounds will be obtained due to there being different carboxylic acid reactive groups in the molecule which can attach to the heterocyclic ring. It is also to be noted that for R* groups which are hydroxy-terminated, such as for example lactic acid or citric acid, it is possible for polyester formation to occur via reaction of the lactic acid moiety (or citric acid) with another lactic acid (or citric acid) moiety. In the case of lactic acid polymerisation of two lactic acid molecules therefore the R* group would be $CH(CH_3)O(CO)CH(CH_3)OH$. Depending on the reaction conditions therefore, a mixture of dye compounds can be obtained, for example in the case of citric acid, there could be two different isomers of these depending on which carboxylic acid group attaches to the heterocyclic ring and compounds formed from a citric acid polymer.

Preferred X groups include Y, SR", halogen (preferably F or Cl), NR"H, NR"2, OR", COOH, SCN, SSO3, SO3, NR1R2, CN, N3, quaternized nitrogen derivatives Q+, wherein R" is C1–C8 alkyl, or aryl and wherein Q, R1 and R2 are as defined above, and oxy-carbonyl and thio-carbonyl groups.

Particularly preferred X groups for use herein are Y, halogen (fluorine and chlorine), quaternized nitrogen derivatives and oxy-carbonyl groups.

A particularly preferred reactive dye compound of the present invention wherein the Y group in formula (I) above is derived from glucose has the following structure Ia:

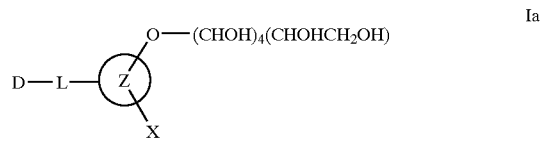

The Y group formed from glucose in structure Ia above may also be polymeric, since when the hydrated form of glucose is prepared via acid hydrolysis of glucose, a polymer may be formed.

Another preferred reactive dye compound of the present invention wherein the Y group is derived from the hydrated form of formic acid in formula (I) above has the following structure Ib. The Y group formed from formic acid can also be polymeric.

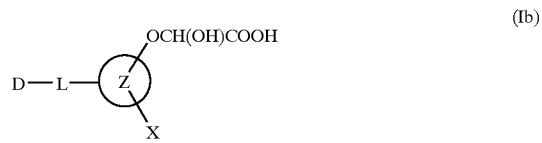

The present invention further relates to processes for the preparation of dyes herein. In general, dyes having the formula (I) can be prepared by reacting suitable precursors of the dye of formula (I) with one another, at least one of which contains a group D—L—Z, wherein D, L and Z are as defined above, and at least one of which contains a Y group wherein Y is as defined above, such as for example the hydrated form of a saccharide material such as sucrose or glucose, or the hydrated form of formic acid, and at least one of which contains an X group. It will be understood by those skilled in the art that in the case where X is halogen, then the halogen is part of the Z group in the starting materials e.g. dichlorotriazine.

For example, dye compounds of the invention having a formula (I) wherein Z is a triazine heterocycle can be prepared by reacting one mole of dichlorotriazine dye, such as those commercially available from BASF under the trade name Procion MX (RTM), with one mole of a suitable reactant containing a Y group such as the hydrated form of a saccharide molecule such as sucrose and glucose, and then reacting the intermediate dye compounds obtained with one mole of a suitable reactant containing an X group. It will be understood by those skilled in the art that when X is halogen, then the halogen is part of the starting material containing the Z group, e.g. dichlorotriazine, and no separate reaction with a reactant containing an X group needs to be carried out. It will also be understood by those skilled in the art that in the case where X is equal to Y (e.g. bis-saccharide compounds) then one mole of dichlorotriazine dye can be reacted with two moles of a suitable reactant containing a Y group. Procion HE (RTM) dyes can also be used as the starting dye in a similar way. Procion HE is a multi-functional reactive dye. When the starting dye compound has multiple reactive groups, for example two reactive groups, one can substitute, for example, one or both of these reactive groups by one or two Y groups, wherein two Y groups in the same molecule may be the same or different.

Dye compounds of the invention having a formula (I) wherein Z is a pyrimidine heterocycle can be prepared by reacting a difluoromonochloro pyrimidine dyes such as those commercially available from Clariant under the trade names Drimalan F (RTM) and Drimarene R or K (RTM), or a trichloropyrimidine dyes such as those commercially available from Clariant under the trade name Drimarene X, with a suitable reactant containing a Y group and then reacting the intermediate dye obtained with a suitable reactant containing an X group. As discussed above for triazines, it will be understood by those skilled in the art that when X is halogen, then the halogen is part of the starting material containing the Z group, e.g. difluoromonochloropyrimidine or trichloropyrimidine, and no separate reaction with a reactant containing an X group needs to be carried out. It will also be understood by those skilled in the art that in the case where X is equal to Y (e.g. bis-saccharide compounds) then one mole of difluoromonochloro pyrimidine dye can be reacted with two moles of a suitable reactant containing a Y group.

Due to the assymmetric nature of the pyrimidine heterocycle, dye compounds of the invention having a formula (I) wherein Z is a pyrimidine heterocycle can also be prepared by reacting a difluoromonochloropyrimidine dye such as those commercially available from Clariant under the tradenames Drimalan F (RTM) and Drimarene R or K (RTM), or a trichloropyrimidine dye such as those commercially available from Clariant under the trade name Drimarene X, with a suitable reactant containing a Y group and then reacting the intermediate dye obtained with a suitable reactant containing an X' group.

Dye compounds of the invention having a formula (I) wherein Z is a quinoxaline heterocycle can be prepared by reacting a dichloroquinoxaline dye such as those commercially available from Dystar under the tradename Levafix E (RTM), with a suitable reactant containing a Y group and then reacting the intermediate dye obtained with a suitable reactant containing an X group. It will be understood by those skilled in the art that when X is halogen, then the halogen is part of the starting material containing the Z group, e.g. dichloroquinoxaline, and no separate reaction with a reactant containing an X group needs to be carried out. It will also be understood by those skilled in the art that in the case where X is equal to Y (e.g. bis-saccharide compounds) then one mole of dichloroquinoxaline dye can be reacted with two moles of a suitable reactant containing a Y group.

It is preferable to carry out the reaction under acidic conditions, preferably at a pH of from about 2 to about 8, preferably from about 3 to about 5. It is also important for the reactant containing the Y group to be added to the Z group slowly, preferably over several hours, preferably 1–5 hours, more preferably 1–3 hours.

Depending upon the reaction conditions (for example, amounts of each starting material, form of each starting material), mixtures of different dye compounds may be obtained in the final product, such mixtures containing for example products formed from further substitution reactions, structural isomers and the like.

Hence according to another aspect of the present invention there is provided the product obtainable by any of the processes detailed herein. In particular there is provided herein the product obtainable by a process wherein the process comprises the steps of reacting a first starting material (preferably one mole) with a second starting material (preferably one mole), the first starting material comprising at least one chromophore, at least one nitrogen-containing heterocycle and a linking group to link each chromophore to each nitrogen-containing heterocycle (for example a Procion MX dye), the second starting material being a compound containing a suitable Y group, such as for example, the hydrated form of a saccharide material, preferably sucrose or glucose.

It is also preferable that the saccharide material is converted to its hydrated form before being reacted with the first starting material. This is preferably done by acid hydrolysis of the saccharide material. Acid hydrolysis can also give polymeric structures such that the Y substituent is polymeric.

The person skilled in the art will appreciate that there are other processes which may be used for manufacturing the compound and products according to the present invention. An alternative preparation process includes, but is not limited to, the following reaction:

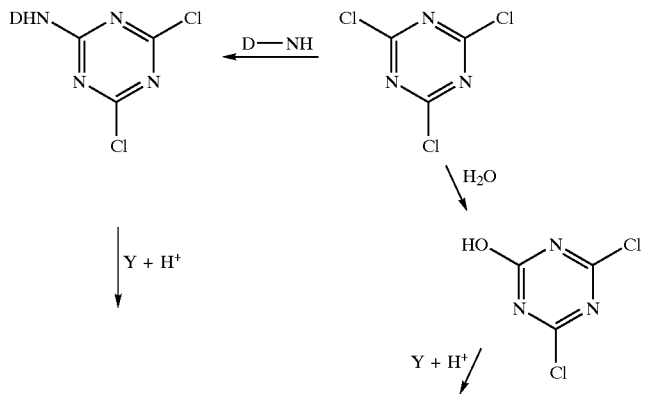

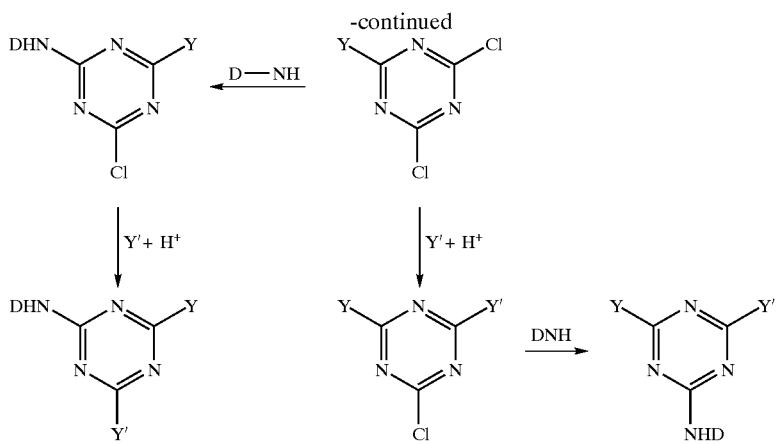

It is preferable that the reaction is carried out at a pH of between about 2 to about 8, preferably about 3 to about 5. It is also preferably that the second starting material is added to the first starting material slowly and dropwise, preferably over several hours, preferably over 1 to 5 hours, more preferably over 1–3 hours.

The dye compounds herein are suitable for dyeing and printing a wide variety of substrates, such as silk, leather, wool, polyamide fibres and polyurethanes, keratin fibres such as hair, and in particular cellulosic materials, such as the natural cellulose fibres, cotton, linen, hemp and the like, paper, and also cellulose itself and regenerated cellulose, wood, and hydroxyl-containing fibres contained in blend fabrics, for example blends of cotton with polyester or polyamide fibres.

The dye compounds of the present invention can be applied and fixed to the substrate in various ways, in particular in the form of a solid mixture, aqueous dye solutions and printing pastes. Thus according to the present invention there is provided a dye composition comprising one or more of the dye compounds described herein together with any carrier material suitable for use in a dye composition.

Preferred dye compositions herein comprise an acidic or neutral buffer material. Any acidic buffer suitable for use in reactive dye compositions can be used herein. An example of a suitable buffer is a mixed phosphate buffer.

When the dye composition herein is in the form of a paste a preferred ingredient is a thickening agent. Any suitable thickening agents suitable for use in reactive dye compositions can be used herein.

When the dye composition is in the form of an aqueous solution or aqueous gel/paste, the dye composition preferably has a pH of from about 2 to about 8. When acidic buffers are used the dye composition preferably has a pH of from about 2 to about 5, especially from about 2 to about 3. When neutral buffers are used, the dye composition preferably has a pH of from about 4 to about 8, preferably from about 6 to about 8.

The dyeing and printing processes which can be used with the dyes herein are conventional processes which are well known and which have been widely described in the technical and patent literature. The dye compounds herein are suitable for dyeing cotton both by the exhaust method (long liquor) and also by various pad-dyeing methods, whereby the goods are impregnated with aqueous, salt-containing or salt-free dye solutions and the dye is fixed after an alkali treatment or in the presence of alkali, if appropriate with the application of heat. The dye compounds herein are also suitable for the cold pad-batch method, in which the dye together with the alkali is applied at the pad-mangle melting point and then fixed by several hours of storage at room temperature. After fixing, the dyeings are thoroughly rinsed with cold and hot water, if appropriate with the addition of an agent acting as a dispersant and promoting the diffusion of the non-fixed portions. The dyes of the present invention are also suitable for use in a number of other processes such as pad-steam and pad-bake and the like. promoting the diffusion of the non-fixed portions.

For cotton blends, a preferred dyeing process is as follows. A mixture of dyes is prepared comprising dyes according to the present invention together with direct dyes. The reactive dyes are fixed at a temperature of 100° C. and the direct dyes are fixed at a temperature of 130° C. Uniform dyeing of the cotton blend is obtained.

Thus in accordance with another aspect of the present invention there is provided a use of the reactive dyes of the present invention for dyeing and printing substrates such as cotton, wool, nylon, silk, keratin, hair, leather, paper and the like. The compounds herein can be used in methods of dyeing all of the substrates listed above by applying an aqueous solution of one or more of the reactive dyes of the present invention to the substrate to be dyed under suitable conditions of pH and temperature.

The following examples serve to illustrate the compounds and compositions of the present invention.

The starting compounds and components given in the examples below can be used in the form of the free acid or in the form of their salts with alkali metal cations. It is to be understood that mixtures of compounds may be obtained in the final product. In the Examples below the starting materials are all commercially available. Procion (RTM) dyes are available from BASF UK, P.O. Box 4, Earl Road, Cheadle Hulme, Cheshire, SK8 6QG, UK, Drimarene (RTM) and Drimalan (RTM) dyes are available from Clariant (Switzerland) Ltd., R&D Dyestuffs, Post Box, Building 88/1007, CH-4002 Basel, Cibacron (RTM) dyes are available from Ciba Specialty Chemicals Inc., R&D, Textile Dyes Division, K-410.312, CH-4002 Basel, and Levafix (RTM) dyes are commercially available from Dystar Textilfarben, GmbH & Co. Deutschland KG, BU-R/F & E, Werk Hochst, Building G834, D-65926 Frankfurt am Main, Germany.

EXAMPLES

The reactive dye compounds of the present examples are prepared as follows. Xg of pure Starting Dye is dissolved in 150 ml of distilled water in a 400 ml flask. The temperature of the reaction system is adjusted and maintained at y° C. The pH of the starting dye solution is adjusted to z using solid sodium carbonate. Ag of sugar is dissolved in 50 ml of distilled water. The pH of this sugar solution is adjusted to b and the sugar acid hydrolysis continues at ambient temperature for 30–35 minutes as shown below.

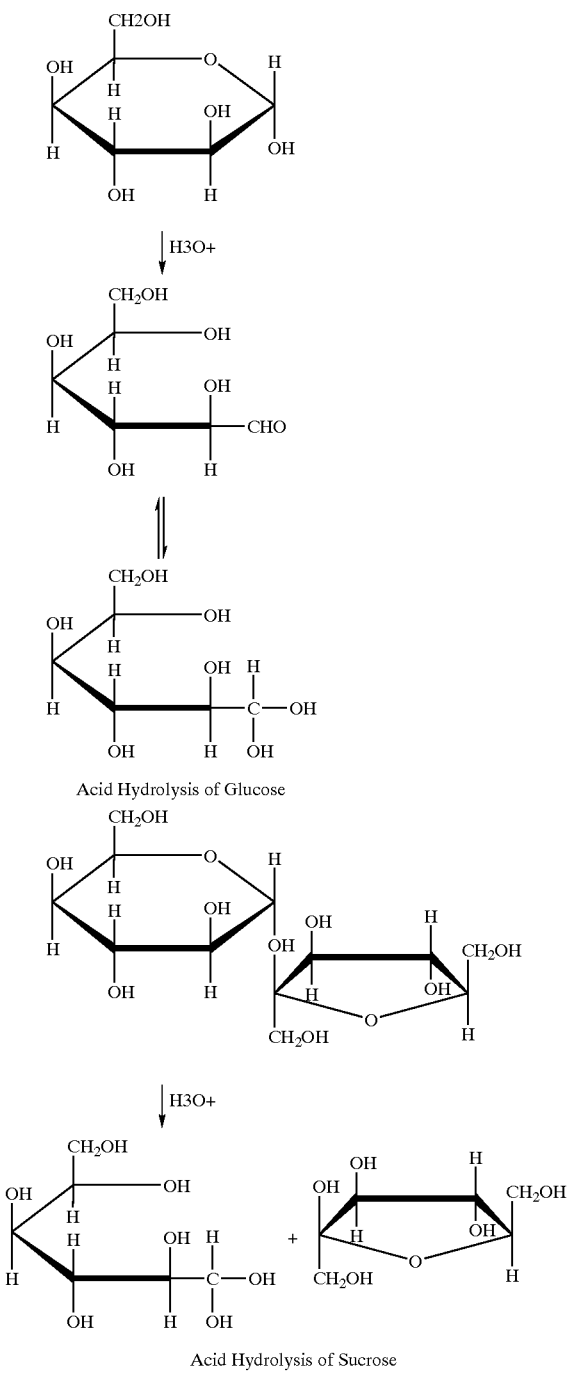

Acid Hydrolysis of Glucose

Acid Hydrolysis of Sucrose

The hydrolysed sugar solution is slowly added into the solution of starting dye. The rate of addition is such that the addition takes around c hours to complete. During the process of addition the temperature of the reaction system is maintained at d° C. After addition of the sugar solution is complete, the reaction is allowed to continue for e hours. The endpoint of the reaction is indicated by the pH of the reaction system remaining constant for more than 5 minutes. At this point the final dye is obtained. Using 6N HCl, the pH of the system is then reduced to below 2.5 to terminate the reaction. KSCN (about 25% of the total solution) is then added to the reaction mixture in order to precipitate the dye product. Filtration using Whatman filter paper is then carried out. The precipitate is then washed with acetone for 5–6 times (about 50 ml of acetone used each time) to obtain the final dye product in fine powder form of f colour. Table I displays Examples 1 to 4 together with reaction conditions y,z,b,c,d and e, amounts of material x and a, colour of final product f, Starting Dye, Final Dye and type of sugar.

A possible synthetic mechanism for the reaction of the Drimarene dyes with glucose in its hydrated form is as follows:

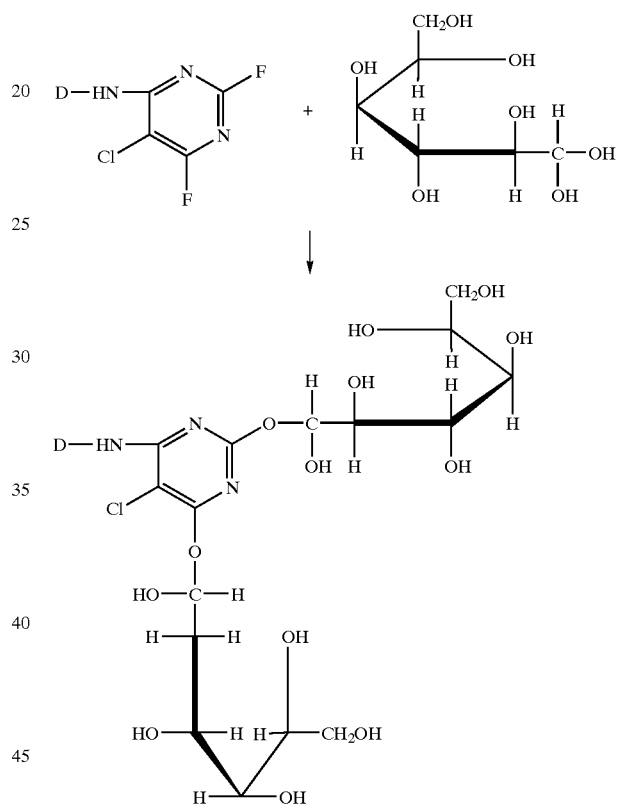

It is also possible for the Y groups in the reaction above to be polymeric as mentioned above, for example in the case of acid hydrolysis of sucrose or glucose.

The compounds prepared according to Examples 1 to 4 and at standard depths all have high Exhaustion Values, high Fixation Values, particularly on cellulosic substrates such as cotton, and show significant improvements in terms of reducing spent dyestuff in effluent, increasing dye affinity to the substrate, increasing the dye-substrate covalent bonding, increasing the ability to dye substrates at room temperature, decreasing the amount of dye that is removed during the post dyeing "soaping off process" and therefore simplifying the post dyeing "soaping off process" traditionally associated with dyeing cotton with fibre reactive dyes and reduction of staining of adjacent white fabrics. In addition, the compounds prepared above provide more intense dyeings and require less levels of salt for dyeing cotton substrates. These advantages can be demonstrated by the following Examples 5 and 6.

Example 5

All dye compounds prepared according to Examples 1 to 4 can be used to dye cotton using the dyeing procedures detailed below. After the cotton dyeing procedure has been carried out a soaping-off process can also be carried out on the cotton fibre.

Cotton Dyeing Procedure

An aqueous dye solution is prepared containing a dye compound according to any of Examples 1 to 4. The dye solution contains 1% on mass of fibre of dye, 80 g/L $Na_2SO_4$ and 5% on mass of fibre of sodium acetate. The cotton fabrics are soaked in water and then the cotton fabrics are dyed in the above dye-bath at pH 7 at 25° C. for 15 minutes. The dyed cotton fabric is then fixed in the dye-bath at pH 11.5 with addition of 30 g/L of trisodium phosphate and dyeing continued at 25° C. for 45 minutes. The dyed fabric is rinsed with water.

In the above dyeing procedure the dye bath for each dye compound is almost totally exhausted (i.e. only slight colour in the dye bath after dyeing), indicating that the compounds prepared according to Examples 1 to 4 each have a high Exhaustion Value (>95%). The Exhaustion Values for each product can be obtained by comparing the photo-absorption of the dyebath liquid before and after dyeing. The Exhaustion Values for Examples 1 to 4 are given in Table A below.

Soaping-off Process

A soaping off process can then be carried out by washing the dyed fabrics with an aqueous solution of Sandozine NIE (2 g/L) (available from Clariant (Switzerland) Ltd., R&D Dyestuffs, Post Box, Building 88/1007, CH-4002 Basel) at 100° C. for 30 minutes.

In the above soaping-off process hardly any colour was removed from the fabric, resulting in an almost colourless soaping liquid, indicating that the compounds prepared according to Examples 1 to 4 each have a high degree of dye-fibre covalent bonding and a high Fixation Value (>95%). The Fixation Values of the dye products prepared according to Examples 1 to 4 are shown in Table A below.

From the Exhaustion and Fixation Values, the Efficiency Values can be calculated.

TABLE A

Exhaustion, Fixation and Efficiency Values for Examples 1 to 4

| Eg. | Exhaustion Value (E %) | Fixation Value (F %) | Efficiency Value (T) |
|---|---|---|---|
| 1 | 99.18% | 98.16% | 97.36 |
| 2 | 98.52% | 97.58% | 96.15 |
| 3 | 97.71% | 94.58% | 92.41 |
| 4 | 99.07% | 98.72% | 97.80 |

The E, F and T values of the dyes according to the present invention are typically higher than many of the commercially available starting materials. In particular, the F and T values of the dyes according to the present invention are significantly higher than those of the commercially available starting materials.

Co3 (International Standards Organisation) Wash Fastness Test

The dyed fabrics are washed with an aqueous solution containing ECE Reference Detergent (5 g/ml) and sodium carbonate (2 g/ml) at 60° C. for 30 minutes.

In the above wash fastness test, no noticeable colour was removed from the cotton fibre and no staining of the white adjacent fibres occurred (using Multiple Fibre adjacent strip supplied by the Society of Dyes and Colourists, Bradford, UK).

Example 6

All dye compounds prepared according to Examples 1 to 4 can be used to dye nylon or wool using the dyeing procedures detailed below. After the nylon/wool dyeing procedure has been carried out a wash-test procedure can be carried out on the dyed fabric to test the wash-fastness of the dye compounds.

Wool/Nylon Dyeing Procedure

The wool/nylon fabric is soaked in a 2% w/w Alcopol-O (40% w/w sodium-d-isooctylsulpho-succinate commercially available from Allied Colloids) solution. The fabric is then dyed for 1 hour at 100° C. and pH 3.5 in a dye-bath containing the following compositions: 1.2% on mass of fibre of dye prepared according to any of Examples 1 to 4, 5% on mass of fibre of sodium acetate, 1% Albegal B (commercially available from Ciba). The dyed wool/nylon fabric was then rinsed with water.

In the above procedure intense dyeings are provided for each of the compounds prepared according to Examples 1 to 4.

Co2 (ISO) Wash Fastness Test Procedure for Wool/Nylon Fabrics

The dyed wool/nylon fabric is washed in an aqueous solution containing 5 g/L of ECE Reference Detergent (commercially available from the Society of Dyers and Colourists, Bradford, UK) at 50° C. for 45 minutes.

In the above wash fastness test, no noticeable colour was removed from the wool fibre and no staining of the white adjacent fibres occurred (using Multiple Fibre adjacent strip supplied by SDC Bradford).

TABLE A

| Eg | Starting Dye | Sugar | x | y | z | a | b | c | d | e | Final Dye | f |
|---|---|---|---|---|---|---|---|---|---|---|---|---|
| 1 | Drimarene Red K4BL | Glucose | 4 g | 30–32° C. | 4–4.5 | 1.2 g | <pH2 | 3–3.5 hr | 30–32° C. | 1–1.5 hrs | Drimarene Red K4BL/Glu | Red |
| 2 | Drimarene Yellow K2R | Glucose | 4 g | 30–35° C. | 4.0–4.5 | 1.2 g | <pH2 | 3–3.5 hr | 30–35° C. | 1–2 hrs | Drimarene Yellow K2R/Glu | Yellow |

TABLE A-continued

| Eg | Starting Dye | Sugar | x | y | z | a | b | c | d | e | Final Dye | f |
|---|---|---|---|---|---|---|---|---|---|---|---|---|
| 3 | Drimarene Blue KBL | Glucose | 4 g | 30–35° C. | 4–4.5 | 1.2 g | <pH2 | 3–4 hrs | 30–35° C. | 1–2 hrs | Remazol Turquoise Blue G/Glu | Blue |
| 4 | Drimarene Red K4BL | Sucrose | 4 g | 40–50° C. | 4–4.5 | 1.2 g | <pH2 | 3–4 hrs | 40–50° C. | 1–2 hrs | Drimarene Red K4BL/Sg | Red |

What is claimed is:

1. A reactive dye compound comprising:
   (a) at least one chromophore moiety;
   (b) at least one nitrogen-containing heterocycle;
   (c) a linking group to link each chromophore moiety to each nitrogen-containing heterocycle; and
   characterized in that at least one nitrogen-containing heterocycle is substituted with at least one Y group wherein Y is derived from a hydrated aldehyde, a hydrated ketone, a hydrated alpha-hydroxy ketone, or the hydrated form of formic acid and linked via one of its oxygen atoms to the nitrogen-containing heterocycle thereby forming a hemiacetal.

2. A reactive dye compound according to claim 1 wherein Y is derived from a hydrated form of an aldehyde or ketone or the hydrated form of formic acid.

3. A reactive dye compound according to claim 1 wherein Y is derived from the hydrated form of a reducing sugar selected from an aldose or a ketose, or the hydrated form of formic acid.

4. A reactive dye compound according to claim 3 wherein said aldose is selected from an aldotriose, an aldotetrose, an aldopentose, an aldohexose, an aldoheptose and an aldooctose, and mixtures thereof.

5. A reactive dye compound according to claim 4 wherein said aldose is an aldopentose selected from ribose, xylose, arabinose, deoxyribose and fructose, and mixtures thereof.

6. A reactive dye compound according to claim 5 wherein said aldose is an aldohexose selected from glucose, galactose, talose, mannose, altrose, allose and rhamnose, and mixtures thereof.

7. A reactive dye compound according to claim 1 wherein Y is derived from glucose, sucrose or fructose or the hydrated form of formic acid.

8. A reactive dye compound according to claim 3 wherein said ketose is selected from an aldotetrulose, an aldopentulose, an aldohexulose, an aldoheptulose, and an aldooctulose, and mixtures thereof.

9. A reactive dye compound according to claim 1 wherein Y is —O—(CHOH)4(CHOHCH2OH).

10. A reactive dye compound according to claim 1 wherein the nitrogen-containing heterocycle is selected from triazine, pyrimidine, quinoxaline, phthalazine, pyridazone and pyrazine.

11. A reactive dye compound according to claim 1 wherein the nitrogen-containing heterocycle is selected from triazine, pyrimidine or quinoxaline.

12. A reactive dye compound according to claim 1 wherein the nitrogen-containing heterocycle is selected from triazine and pyrimidine.

13. A reactive dye compound according to claim 1 wherein the linking group is selected from NR, N(C=O)R, N(SO2)R where R is selected from H or C1–C4 alkyl which can be substituted by halo, hydroxy, cyano, C1–C4 alkoxy, C2–C5 alkoxycarbonyl, carboxyl, sulfamoyl, sulfo and sulfato.

14. A reactive dye compound according to claim 13 wherein the linking group is NR.

15. A reactive dye compound according to claim 14 wherein R is H or C1–C4 alkyl.

16. A reactive dye compound according to claim 1 wherein the nitrogen-containing heterocycle is additionally substituted with one or more X substituents, wherein X is independently selected from Y, thio-derivatives, halogen (preferably fluorine and chlorine), amines, alkoxy groups, carboxylic acid groups, CN, $N_3$, quaternized nitrogen derivatives (Q+) and oxy- or thio-carbonyl derivatives having the formula —A(CO)R* wherein A is selected from O or S, where R* is an organic residue which contains at least one nucleophilic group, wherein the nucleophilic group is preferably selected from OH, $NH_2$, SH, COOH, —N=, $NHR^1$ and $NR^1R^2$ wherein $R^1$ and $R^2$ may be the same of different and may be selected from $C_1$–$C_4$ alkyl, preferably Y or halogen.

17. A reactive dye having the formula (I):

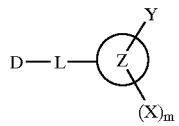

wherein

D is a chromophore group;

L is a linking moiety selected from NR, N(C=O)R, N(SO2)R;

R is H or $C_1$–$C_4$ alkyl which can be substituted by halogen, hydroxyl, cyano, $C_1$–$C_4$ alkoxy, $C_2$–$C_5$ alkoxycarbony, carboxyl, sulfamoyl, sulfo, sulfato;

Z is a nitrogen-containing heterocycle;

Y is derived from a hydrated aldehyde, a hydrated ketone, a hydrated alpha-hydroxy ketone, or the hydrated form of formic acid and linked via one of its oxygen atoms to the nitrogen-containing heterocycle thereby forming a hemiacetal;

X is selected from Y (i.e. bis-saccharide compounds), thio-derivatives, halogen (preferably fluorine and chlorine), amines, alkoxy groups, carboxylic acid groups, CN, $N_3$, quaternized nitrogen derivatives (Q+) and oxy- or thio-carbonyl derivatives having the formula —A(CO)R* wherein A is selected from O or S, where R* is an organic residue which contains at least one nucleophilic group, wherein the nucleophilic group is preferably selected from OH, $NH_2$, SH, COOH, —N=, $NHR^1$ and $NR^1R^2$ wherein $R^1$ and $R^2$ may be the same of different and may be selected from $C_1$–$C_4$ alkyl; and m is an integer of from 1 to 4; and salts and esters thereof.

18. A method of dyeing a cellulosic substrate, comprising contacting the cellulosic substrate with a compound according to claim 1.

19. A method of dyeing wool, comprising contacting the wool with a compound according to claim 1.

20. A method of dyeing a polyamide substrate, comprising contacting the polyamide substrate with a compound according to claim 1.

21. A method of dyeing silk, comprising contacting the silk with a compound according to claim 1.

22. A method of dyeing keratin, comprising contacting the keratin with a compound according to claim 1.

23. A method of dyeing leather, comprising contacting the leather with a compound according to claim 1.

24. Process for the preparation of a compound according to claim 1 comprising the steps of reacting a first starting material with a second starting material, the first starting material comprising at least one chromophore, at least one nitrogen-containing heterocycle linked to the chromophore via a linking group L, the second starting material being a compound containing a Y group.

25. Process according to claim 24 wherein the reducing sugar is selected from sucrose, glucose and mixtures thereof.

26. Process according to claim 24 wherein the process is carried out at a pH of from about 2 to about 8.

27. Process according to claim 24 wherein the second starting material is added to the first starting material slowly.

28. Product obtainable by the process according to claim 24.

29. A dye composition comprising the compound of claim 1.

30. A dye composition according to claim 29 wherein the composition is in the form of a solid mixture and further comprises an acid or neutral buffer.

31. A dye composition according to claim 29 wherein the composition is in the form of a liquid and further comprises water and an acid or neutral buffer.

32. A dye composition according to claim 29 wherein the composition is in the form of a paste and further comprises water, thickening agent and an acid or neutral buffer.

33. A dye composition according to claim 29 wherein the pH of the composition is in the range of from about 2 to about 5, when an acidic buffer is present, and in the range of from about 4 to about 8, when a neutral buffer is present.

34. A dye composition comprising the product of claim 24.

35. A dye composition according to claim 34 wherein the composition is in the form of a solid mixture and further comprises an acid or neutral buffer.

36. A dye composition according to claim 34 wherein the composition is in the form of a liquid and further comprises water and an acid or neutral buffer.

37. A dye composition according to claim 34 wherein the composition is in the form of a paste and further comprises water, thickening agent and an acid or neutral buffer.

38. A dye composition according to claim 34 wherein the pH of the composition is in the range of from about 2 to about 5, when an acidic buffer is present, and in the range of from about 4 to about 8, when a neutral buffer is present.

\* \* \* \* \*